United States Patent [19]

Maignan et al.

[11] Patent Number: 5,126,453
[45] Date of Patent: Jun. 30, 1992

[54] PROCESS FOR THE PREPARATION OF 6-PIPERIDINO-2,4-DIAMINO PYRIMIDINE-3-OXIDE AND NOVEL COMPOUNDS

[75] Inventors: Jean Maignan, Tremblay-les-Gonesse; Serge Restle, Aulnay-sous-Bois; Gerard Lang, Saint-Gratien, all of France

[73] Assignee: L'Oreal, Paris, France

[21] Appl. No.: 636,126

[22] Filed: Dec. 31, 1990

Related U.S. Application Data

[62] Division of Ser. No. 225,819, Jul. 29, 1988, Pat. No. 4,985,563.

[30] Foreign Application Priority Data

Jul. 31, 1987 [LU] Luxembourg ............... 86960

[51] Int. Cl.⁵ .................................. C07D 239/28
[52] U.S. Cl. ............................. 544/320; 544/323
[58] Field of Search ......................... 544/320, 323

[56] References Cited

U.S. PATENT DOCUMENTS 3,382,247 5/1968 Anthony et al. ............... 260/256.4
3,910,928 10/1975 McCall et al. .................... 544/320

Primary Examiner—Johann Richter
Attorney, Agent, or Firm—Fleit, Jacobson, Cohn, Price, Holman & Stern

[57] ABSTRACT

In a first stage of a process for the preparation of 6-piperidino-2,4-diaminopyrimidine-3-oxide at least one of the two amino groups of a compound having formula (1):

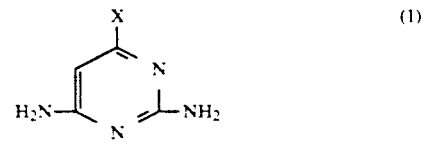

where X represents a halogen atom or OH group, is protected by an addition reaction with an isocyanate having formula:

$$R-N=C=O$$

In this formula R represents an alkyl group, or one of the amino groups. The resulting urea derivative is then oxidized to produce the corresponding N-oxide which is then reacted with piperidine. The protective group(s) are then eliminated by reaction with an organic or inorganic base.

1 Claim, No Drawings

PROCESS FOR THE PREPARATION OF 6-PIPERIDINO-2,4-DIAMINO PYRIMIDINE-3-OXIDE AND NOVEL COMPOUNDS

This is a divisional of application Ser. No. 225,819, filed Jul. 29, 1988, now U.S. Pat. No. 4,985,563.

BACKGROUND OF THE INVENTION

The present invention relates to the preparation of 6-piperidino-2,4-diaminopyrimidine-3-oxide, better known under its international generic trade name "Minoxidil".

"Minoxidil" is known for its antihypertensive properties and for its application in the treatment of alopecia.

Several processes for the preparation of 6-piperidino-2,4-diaminopyrimidine-3-oxide are already known. U.S. Pat. No. 3 382 247 describes a process which consists in preparing, in a first stage, 6-chloro-2,4-diamino pyrimidine from 6-hydroxy-2,4-diaminopyrimidine by treatment with phosphorus oxychloride. Reaction of a phenolate on 6-chloro-2,4-diaminopyrimidine produces 6-phenoxy-2,4-diaminopyrimidine. This latter, is oxidized to the corresponding 3-nitro-oxide by meta-chloroperbenzoic acid (MCPA). After reaction with piperidine, "Minoxidil" is isolated.

GB-A-2 032 434 describes a process for the preparation of "Minoxidil" consisting in preparing, in a first stage, the O-tosylate of 6-hydroxy-2,4-diamino pyrimidine, oxidizing the latter to a corresponding oxide by the action of MCPA and finally treating the tosylate N-oxide with piperidine.

According to U.S. Pat. No. 3 910 928 the pyrimidine ring is synthesized from 3-cyaniminopropionitrile.

In the first two syntheses the amine groups in the 2- and 4- positions of the chloro- or hydroxy diaminopyrimidine remain free.

The applicant has discovered a novel process for the preparation of 6-piperidino-2,4-diaminopyrimidine-3-oxide or "Minoxidil", following a simple and less onerous procedure when compared with state of the art processes. This process forms one object of the invention.

Thus one object of the invention is a novel process for the preparation of "Minoxidil".

Another object of the invention is novel products prepared during this process.

Further objects of the invention will become apparent from the following description and examples.

In one aspect, the invention consists in a process for the preparation of 6-piperidino-2,4-diamino pyrimidine-3-oxide wherein, in a first stage, at least one of the amino groups of a compound having formula 1:

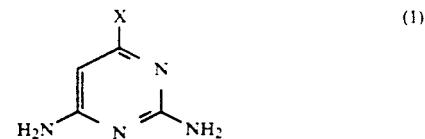

where X represents a halogen atom or OH group, is protected by an isocyanate having formula:

where R represents an alkyl group preferably having 1 to 6 carbon atoms, with one of the amino groups of the compound having formula (1); addition resulting in a urea derivative which is subsequently oxidized to transform it into the corresponding N-oxide, said N-oxide then being reacted with piperidine then undergoing an elimination reaction to remove the protective group(s) by treatment with an organic or inorganic base.

In another aspect the invention consists in a novel compound having the formula:

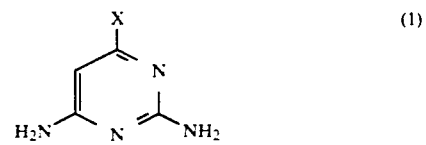

wherein:

X represents OH,Cl,O-tosyl,O-benzenesulfonyl;

$R_1$ and $R_2$ are independent of each other and represent a hydrogen atom or the group RNHCO—, where R represents a $C_1$ to $C_6$ alkyl, and $R_1$ and $R_2$ do not simultaneously represent hydrogen; and n equals 0 or 1, including their tautomeric or isomeric forms.

DESCRIPTION OF THE INVENTION

The invention process can be especially well illustrated by the following reaction schemes.

SCHEME A

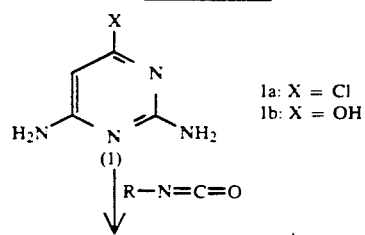

1a: X = Cl
1b: X = OH

SCHEME A

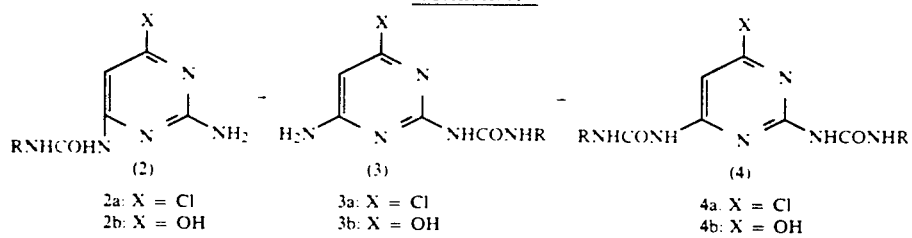

| (2) | (3) | (4) |
|---|---|---|
| 2a: X = Cl | 3a: X = Cl | 4a: X = Cl |
| 2b: X = OH | 3b: X = OH | 4b: X = OH |

SCHEME B

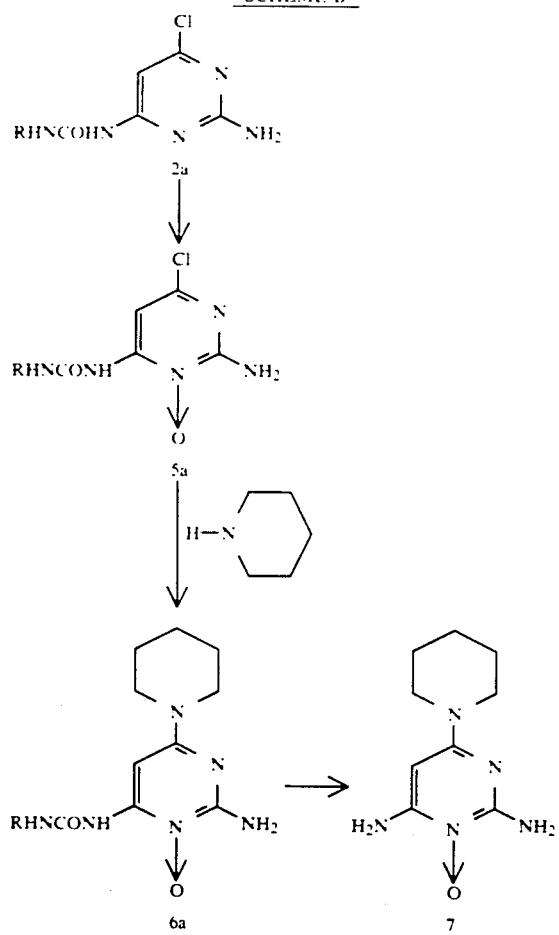

SCHEME C

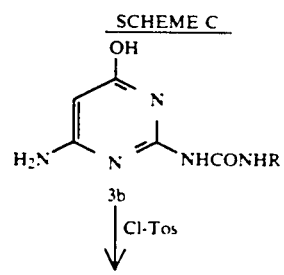

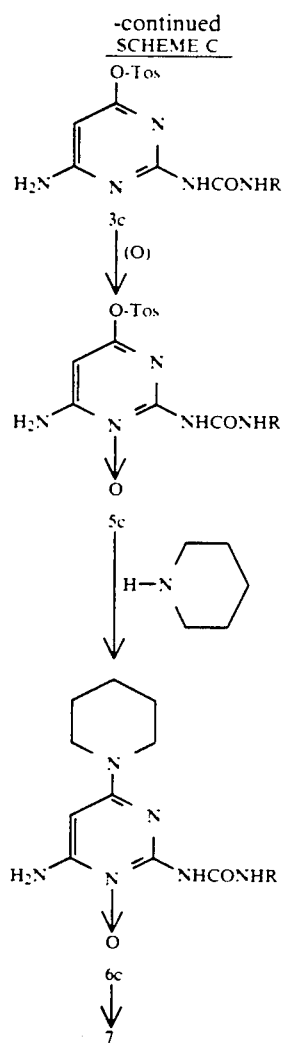

SCHEME A

In the first stage of the inventive process a mixture of mono-ureas having formula 2a and 3a is obtained from compound 1a. The mixture also contains the diurea having formula 4a, the quantity depending on the reaction temperature and the number of equivalents of isocyanate used.

The reaction can be selectively driected towards formation of urea 2a or 3b by using aprotic solvents, in particular dimethylsulfoxide (DMSO), dimethylformamide (DMF) or N-methylpryrrolidone. Urea 2a or 3b is formed depending on whether the starting compound is the chloro, 1a or hydroxy, 1b compound, respectively.

The small amount of diurea 4a or 4b formed can be readily eliminated by filtration of the reaction mixtures at room temperature due to the large solubility difference between mono- or diureas in the medium used.

This first stage is of particular interest since it uses commercially obtainable, readily accessible products.

Butylisocyanate produces results of particular interest especially regarding the reaction yield.

Using a solvent such as tetrahydrofuran in the first stage preferentially yields the urea 3a from compound 1a, particularly if butylisocyanate is used.

SCHEME B

During the second stage the monourea of formula 2a, whose 4-position amino group has been blocked, is preferentially oxidized. This urea is more easily oxidizable at the 3-position. Heterogeneous phase reaction may in particular be employed, using a mixture of a chlorinated solvent such as dichloromethane in the presence of about 5 to 30%, preferably 10% formic acid, adding an excess of oxygenated water of 2 to 5 equivalents with respect to the starting compound, and preferably 2.5 equivalents. Quantitative transformation of urea 2a into the corresponding 3-N-oxide is obtained. Very good results are also obtained with dioxan in place of dichloromethane.

The reaction is carried out at a temperature of between 0° and 70° C., preferably between 35° and 65° C.

It has been established that, using these conditions, usual chromatographic means detect neither secondary derivatives nor degradation products in any considerable quantities.

SCHEME C

Another variant of stage 2 according to the invention consists in transforming the hydroxylated monourea 3b into the corresponding tosylate 3c by known methods, compound 3c then being oxidized to a 3-N-oxide (5c). Mono-urea 3b is preferentially formed by action of an isocyanate on the starting compound 1b solubilized in N-methylpyrrolinone.

It should be noted that the tosylate or benzene sulfonate can be synthesized, in a first stage, from compound (1b). In a second stage, the tosylate or benzyl sulfonate is reacted with an isocyanate to obtain the mono-urea sulfonates (2b) and/or (3b).

Compounds (5a) or (5c) are reacted in a subsequent stage with piperidine, preferably in excess, and are transformed into the mono-ureas 6a or 6c. In this case too, yields are quantitative and of particular interest.

Finally, the last stage involves elimination of the protective urea group by treatment with a strong mineral or organic base, in particular potash, soda or sodium methylate but preferably potash.

This process is of particular interest insofar as it can also be used for a mixture of compounds 2a, 3a and 4a.

The process transforms a compound having formula (1) into a mono-urea by a simple addition reaction of an amino group or an isocyanate.

Mono-ureas thus obtained are far more soluble in normal solvents than the starting compounds and lend themselves particularly well to oxidation reactions to obtain the corresponding 3-N-oxide.

The mono-ureas can, in particular, be used for selective oxidation.

A particular preferred reaction consists in going via the intermediate 6-chloro-2,4-diamino pyrimidine using oxygenated water as the preferred oxidant for the oxidation state. The use of oxygenated water carries the additional advantages of reducing costs and avoiding the problem of eliminating metachloroperbenzoic acid.

Intermediate compounds in the form of the N-oxide chlorinated in the 6-position correspond to the formula:

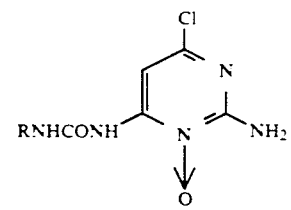

These are of particular interest because of their solubility for treatment with pyrimidine.

Transformation of the urea into the corresponding amine in the final stage is a simple reaction since it is effected by the action of a mineral or organic base.

The intermediate ureas prepared during the inventive process constitute the novel products which are objects of the invention.

These compounds correspond to the following formula:

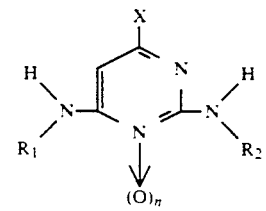

where:

X represents an OH, Cl, O-tosyl, O-benzenesulfonyl or a piperidine group;

$R_1$ and $R_2$ are independent of each other and represent hydrogen or an RNHCO—group, where R represents a $C_1$ to $C_6$ alkyl group, and $R_1$ and $R_2$ do not simultaneously represent hydrogen; and n equals 0 or 1.

The tautomeric or isomeric forms of these compounds are also included within the scope of the invention The following examples are intended to illustrate the invention without in any way limiting its scope.

EXAMPLE 1

Synthesis of 6-piperidino-2,4-diaminopyrimidine-3-oxide

Stage 1

Preparation of

N-(2-amino-6-chloro-4-pyrimidinyl),N'- butylurea 8.6 cm³ butylisocyanate was added to a suspension of 5 g 6-chloro-2,4-diaminopyrimidine in 50 cm³ DMSO. The reaction medium was maintained at 80° C. until it was shown by TLC that the starting compound had disappeared.

Following hydrolysis of the reaction medium, the product was extracted with ethyl acetate. The organic phase was washed, dried and concentrated under reduced pressure.

5.1 g of product was obtained which was recrystallized from ethyl acetate.

N-(2-amino-6-chloro-4-pyrimidinyl),N'-butylurea crystallized in the form of white crystals melting at 227° C.

The $^1$H NMR spectrum agreed with the expected structure.

Stage 2

Preparation of

N(2-amino-3-oxide-6-chloro-4-pyrimidinyl), N'-butylurea 2.17 g MCPB was added to a suspension of 2.8 g previously prepared N-(2-amino-6-chloro-4-pyrimidinyl), N'-butylurea in a mixture of 100 cm$^3$ alcohol and 15 cm$^3$ water.

The temperature was maintained at 20° C. and the reaction progress followed using TLC.

After transformation of the starting compound the alcohol was evaporated off under reduced pressure and the residue taken up into water supplemented with sodium bicarbonate.

After vigorously agitating the aqueous phase for half an hour the precipitate was filtered, washed with plenty of water and dried.

2.5 g of white crystals melting at 195°-196° C. were obtained whose $^1$H NMR spectrum agreed with the expected structure.

Stage 2a

Preparation of

N-(2-amino-3-oxide-6-chloro-4-pyrimidinyl), N'-butylurea Oxidation with oxygenated water 1.9 cm$^3$ oxygenated water was added to a solution of 1.9 g previously prepared N-(2-amino-6-chloro-4-pyrimidinyl),N'-butylurea in 40 cm$^3$ dichloromethane and 4 cm$^3$ formic acid. The solution was kept at 40° C. for 4 hours. After transformation of the starting compound, the dichloromethane was evaporated off under reduced pressure and the residue taken up in water. The precipitate was filtered, washed with plenty of water and dried. 1.4 g of crystals of the desired product were obtained. They melted at 194°-195° C.

Stage 3

Preparation of

N-(6-piperidino-2-amino-3-oxide-4-pyrimidinyl), N'-butyl urea

A suspension of 1 g of previously prepared N-(2-amino-3-oxide-6-chloro-4-pyrimidinyl),N'-butylurea in 10 cm$^3$ piperidine was heated for 1 hour at 100° C.

The reaction medium was poured over ice water and the precipitate obtained filtered, dried and recrystallized from methanol.

0.950 mg N-(6-piperidino-2-amino-3-oxide -4-pyrimidinyl),N'-butylurea was obtained.

Stage 4

Preparation of 6-piperidino-2,4-diaminopyrimidine-3-oxide

A solution of 1 g N-(6-piperidino-2-amino -3-oxide-4-pyrimidinyl),N'-butylurea in a mixture of 50 cm$^3$ isopropanol and 25 cm$^3$ 10 N potash was maintained at 80° C. until the starting compound had disappeared.

The isopropanol was evaporated off under reduced pressure and the desired product crystallized out of the aqueous phase. This latter was diluted with 50 cm$^3$ water and the product was filtered off.

Recrystallization from methanol produced 550 mg 6-piperidino-2,4-diaminopyrimidine-3-oxide having a melting point of 260° C.

In the above example, each intermediate compound was purified by recrystallization. The synthesis can be carried out to the last stage without purifying the intermediates.

Given below are the amounts obtained in each of these stages.

EXAMPLE 1A

Stage 1

Preparation of

N-(2-amino-6-chloro-4-pyrimidinyl),N'-butylurea 100 g 6-chloro-2,4-diaminopyrimidine in solution in 1 liter N-methyl pyrrolidone were heated with 95 cm$^3$ n-butylisocyanate at 95° C. for 9 hours. At the end of the reaction the reaction medium was poured into 5 liters water. The precipitate obtained was filtered and dried.

164 g crude N-(2-amino-6-chloro-4-pyrimidinyl), N'-butylurea, containing about 20% of its isomer, was obtained.

Stage 2

Preparation of

N-(2-amino-3-oxide-6-chloro-4-pyrimidinyl), N'-butylurea 175 cm$^3$ 110 vol oxygenated water was added to a suspension of 150 g of the crude product obtained in the preceding stage in 2 liters dioxan and 200 cm$^3$ formic acid. The mixture was kept at 60° C. for 48 hours. After filtering over cellulose acetate, the excess of oxygenated water was neutralized by addition of an aqueous hydrogen sulfite solution. The dioxan was then eliminated by vacuum evaporation. The N-oxide obtained in crystalline form at room temperature was filtered, water washed and dried.

92 g N-(2-amino-3-oxide-6-chloro-4-pyrimidinyl), N'-butylurea was obtained.

In this particular operation, filtration over cellulose acetate was carried out at 40° C., thus eliminating the majority of the 2-position isomer which does not oxidize under these conditions.

Stage 3

Preparation of

N-(6-piperidino-2-amino-3-oxide-4-pyrimidinyl), N'-butyl urea

A suspension of 90 g N-(2-amino-3-oxide-6-chloro-4-pyrimidinyl),N'-butylurea from the preceding stage in 700 cm$^3$ piperidine was agitated at 50° C. for 4 hours. The medium became progressively more homogeneous. Part of the piperidine hydrochlorate precipitated at room temperature was eliminated by filtration. The solution was concentrated to a final volume of 500 cm$^3$ and then poured over 1.5 liter ice water under strong agitation.

97 g of N-(6-piperidino-2-amino-3-oxide -4-pyrimidinyl),N'-butylurea was obtained.

Stage 4

Preparation of 6-piperidino-2,4-diaminopyrimidine-3-oxide

A solution of 90 g of the product obtained in the preceding stage in 750 cm³ butanol and 10 cm³ water was heated to 100° C. under agitation. 20 g pelletized potash was added in small portions. The temperature was maintained for 3 hours. After cooling, the solution was washed with water and the butanol eliminated by evaporation under reduced pressure. The product obtained was then agitated in 200 cm³ ethyl acetate at room temperature; in this way a majority of the impurities was extracted.

45 g of 6-piperidino-2,4-diaminopyrimidine-3-oxide was obtained which was recrystallized from an acetonitrile-methanol mixture.

EXAMPLE 2

Synthesis of 6-piperidino-2,4-diaminopyrimidine-3-oxide from 2,4-diaminohydroxy-6-pyrimidine Stage 1

Synthesis of N-(4-amino-6-hydroxy-2-pyrimidinyl) N'-cyclohexylurea

A solution of 10 cm³ cyclohexyl isocyanate in 50 cm³ N-methylpyrrolidone was added dropwise to a suspension of 10 g 2,4-diamino-6-hydroxypyrimidine in about 100 cm³ N-methyl pyrrolidone at 60° C. Following addition the mixture was heated for 3 hours. A further 2 cm³ cyclohexyl isocyanate was added and the reaction temperature raised to 90° C. for 2 hours. After verification by thin layer chromatography that the starting compound had completely disappeared, a mixture of 5 cm³ acetic acid in 20 cm³ water was added and the reaction medium was left overnight at room temperature.

The solution was poured over 1 l water and stirred for about an hour. The desired product was filtered and after drying 17 g of a white powder was obtained whose capillary melting point was 236° C.

| Elemental analysis $C_{11}H_{17}N_5O_2$ | | | | |
|---|---|---|---|---|
| | C % | H % | N % | O % |
| Calculated value: | 52.57 | 6.82 | 27.87 | 12.73 |
| Found value | 51.85 | 6.75 | 27.53 | 12.55 |

Stage 2

Synthesis of N-(6-tolylparaoxysulfonyl-4-amino-2-pyrimidinyl), N'-cyclohexylurea A solution of 1 N soda was added dropwise to a suspension of 8 g N-(4-amino-6-hydroxy-2-pyrimidinyl),N'-cyclohexylurea and 12.2 g toluene-para-sulfonyl chloride in a mixture of 120 cm³ water and 40 cm³ acetone at 40° C. The reaction was followed by continuously monitoring the pH of the reaction medium in order to assure that the soda added was rapidly consumed.

Once the reaction had stopped, thin layer chromatography was used to verify that all the starting compound had disappeared and a further 100 cm³ dilute soda was added in order to eliminate the excess of toluene-para-sulfonyl chloride.

The precipitate thus obtained was filtered and washed with plenty of water (until the washings were neutral). After drying 8.3 g of product was obtained which melted at 203°–205° C.

| Elemental analysis $C_{18}H_{23}N_5O_4S$ | | | | | |
|---|---|---|---|---|---|
| | C % | H % | N % | O % | S % |
| Calculated value: | 53.32 | 5.72 | 17.27 | 15.78 | 7.91 |
| Found value | 53.11 | 5.65 | 17.31 | 15.63 | 7.88 |

Stage 3

Synthesis of N-(6-tolylparaoxysulfonyl-4-amino-3-oxide-2-pyrimidinyl) N'-cyclohexylurea 20 cm³ formic acid and 6 cm³ 110 vol oxygenated water were added to a suspension of 3 g N-(-6-tolyl paraoxysulfonyl-4-amino-2-pyrimidinyl),N'-cyclohexylurea in 100 cm³ dioxan and temperature brought to 55° C. for about 1 hour (the starting compound went into solution). 3 cm³ 110 vol oxygenated water was added and the temperature maintained for a further hour.

The reaction medium was poured over 300 cm³ ice water and the precipitate formed filtered and washed with plenty of water.

After drying a white powder was obtained whose 80 MHz ¹H NMR spectrum agreed with the expected structure and whose melting point was 215° C. (the product started to turn brown at about 130° C.).

Stage 4

Synthesis of N-(6-piperidino-4-amino-3-oxide-2-pyrimidinyl), N'-cyclo hexylurea 0.5 cm³ piperidine was added to a solution of 1.5 g N-(6-tolylparaoxysulfonyl-4-amino-2-pyrimidinyl), N'-cyclohexylurea in 50 cm³ THF. The mixture was agitated for ½ hour at room temperature then the temperature raised to 60° C. for 1 hour. At the end of the reaction the medium was poured into water and extracted with ethyl acetate.

The crude reaction product was purified by silica gel chromatography (eluant+$CH_2Cl_2$—MeOH) and 750 mg of a pink-tinged white powder was obtained whose 80 Hz ¹NMR spectrum agreed with the expected structure and melted at 183°–185° C.

Stage 5

Preparation of 6-piperidino-2,4-diaminopYrimidine-3-oxide

N-(6-piperidino-4-amino-3-oxide-2-pyrimidinyl), N'-cyclohexylurea was reacted under conditions described in stage 4 of example 1.

The reaction time for removal of the urea function in the 2-position is longer than that with the urea in the 4-position (example 1).

We claim:

1. A compound having the formula:

11

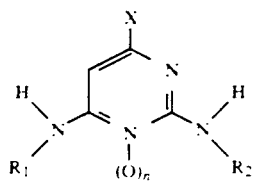

wherein:
X represents OH, Cl, O-tosyl, O-benzene sulfonyl;
$R_1$ and $R_2$ are independent of each other and represent a hydrogen atom or the group RNHCO—, where R represents $C_1$ to $C_6$ alkyl, and $R_1$ and $R_2$ do not represent simultaneously hydrogen; n equals 0 or 1.

* * * * *

12

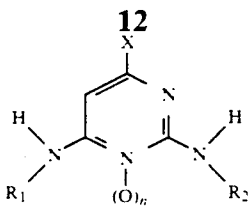

wherein:
X represents OH, Cl, O-tosyl, O-benzene sulfonyl;
$R_1$ and $R_2$ are independent of each other and represent a hydrogen atom or the group RNHCO—, where R represents $C_1$ to $C_6$ alkyl, and $R_1$ and $R_2$ do not represent simultaneously hydrogen; n equals 0 or 1.

* * * * *